(12) United States Patent
Nakamura et al.

(10) Patent No.: US 6,646,163 B2
(45) Date of Patent: Nov. 11, 2003

(54) METHOD FOR PRODUCING HIGH PURITY XYLYLENEDIAMINE

(75) Inventors: Kenichi Nakamura, Niigata (JP); Kazuhiko Amakawa, Niigata (JP); Takuji Shitara, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/187,020

(22) Filed: Jul. 2, 2002

(65) Prior Publication Data

US 2003/0013917 A1 Jan. 16, 2003

(30) Foreign Application Priority Data

Jul. 16, 2001 (JP) .......................................... 2001-215006

(51) Int. Cl.$^7$ ............................................ C07C 211/27
(52) U.S. Cl. ........................ 564/388; 564/395; 564/415
(58) Field of Search ................................ 564/388, 395, 564/415

(56) References Cited

U.S. PATENT DOCUMENTS 3,069,469 A    12/1962   Wilkes
6,476,269 B2 * 11/2002   Nakamura et al. .......... 564/388

FOREIGN PATENT DOCUMENTS

| EP | EP 1 113 001 A2 | 7/2001 |
| EP | EP 1 193 244 A2 | 4/2002 |
| EP | EP 1 193 247 A2 | 4/2002 |

OTHER PUBLICATIONS

Chem Abstract 1987:536278.Pryanikov et al, 1987.*
European Search Report, transmitted Oct. 16, 2002, for EP 02 01 4611.

* cited by examiner

Primary Examiner—Samuel Barts
(74) Attorney, Agent, or Firm—Antonelli, Terry, Stout & Kraus, LLP

(57) ABSTRACT

In a method for producing xylylenediamine by hydrogenating phthalonitrile separated from a gas produced by causing xylene to react with ammonia and oxygen-containing gas in the presence of a catalyst, (1) the gas is brought into contact with an organic solvent to trap phthalonitrile; (2) a liquid in which phthalonitrile is trapped is distilled, to thereby recover phthalonitrile and the organic solvent from the top of the column and separate at the bottom of the column impurities having boiling points higher than that of phthalonitrile; (3) the organic solvent is recovered from the top of the column and liquefied phthalonitrile of high purity is recovered at the bottom of the column; and (4) the phthalonitrile is hydrogenated after mixing with liquid ammonia and at least one solvent selected from aromatic hydrocarbon and saturated hydrocarbon. Thus, high-purity phthalonitrile is produced at high yield industrially efficiently.

6 Claims, 1 Drawing Sheet

METHOD FOR PRODUCING HIGH PURITY XYLYLENEDIAMINE

BACKGROUND OF THE INVENTION

1. Field of the Invention

The present invention relates to a method for producing xylylenediamine by hydrogenating phthalonitrile obtained through ammoxidation of xylene.

Xylylenediamine is useful as a raw material of, for example, polyamide resins or epoxy curing agents, and as an intermediate material for producing isocyanates.

2. Background

Xylylenediamine is produced by hydrogenation of phthalonitrile in the presence of ammonia.

For producing phthalonitrile, xylene is reacted through ammoxidation with ammonia and molecular oxygen in the presence of a catalyst.

A method of reacting, in the presence of a catalyst, an organic-substituent-containing carbon-ring or heterocyclic compound with ammonia and an oxygen-containing gas is called ammoxidation, and is generally employed for producing nitrile compounds through a vapor-solid fluidized catalytic process.

A variety of methods for separating a nitrile compound from a gas produced through ammoxidation have already been known. For example, *Chemical Engineering* (Nov. 1971, pp. 53–55) discloses a method for depositing isophthalonitrile, in which a gas produced through ammoxidation of m-xylene so as to produce isophthalonitrile is introduced into a scrubber and is cooled with water, then the obtained slurry of isophthalonitrile is introduced into a filter, to thereby isolate crystals of isophthalonitrile, and the crystals are dehydrated and dried, to thereby yield a final product.

Process Handbook (published in 1976, edited by The Japan Petroleum Institute) discloses the MGC-Badger isophthalonitrile process, in which isophthalonitrile contained in a gas produced through reaction is trapped by an organic solvent; the isophthalonitrile-trapped liquid is transferred to a solvent recovery column for the removal of solvent from the column top and crude isophthalonitrile is recovered from the bottom; and the crude isophthalonitrile is supplied to a rectification column, whereby purified isophthalonitrile is recovered from the column top.

In the method described in *Chemical Engineering* in which a gas produced through ammoxidation of m-xylene so as to produce isophthalonitrile is introduced into a scrubber and is cooled with water, by-products generated during ammoxidation are also deposited with isophthalonitrile. Thus, an additional purification step is required in order to obtain isophthalonitrile of high purity.

The method described in Process Handbook employing trapping by an organic solvent enables obtaining of high-purity isophthalonitrile. However, the method poses the following problems among others. (1) When a sublimable high-melting-point substance such as isophthalonitrile is separated through distillation under reduced pressure and removed from the top of the distillation column, isophthalonitrile may be solidified due to overcooling, since the condensation temperature and the melting point are close to each other in a high vacuum. (2) Due to high-temperature operation, vapor pressure of isophthalonitrile becomes high, and isophthalonitrile migrates to a vacuum evacuation system, to thereby deposit crystals thereof and cause plugging. (3) To prevent this, there must be taken measures including provision of a scrubber between the condensation section and the vacuum evacuation system. (4) Generally, in the presence of impurities such as high-boiling-point by-products generated during ammoxidation, ammoxidation catalyst, and metallic components, isophthalonitrile is unstable to heat and readily undergoes undesirable change or deterioration. Thus, when isophthalonitrile is exposed to high temperature during distillation, significant portions of isophthalonitrile are lost.

Then m-xylylenediamine is not produced efficiently by hydrogenation of isophthalonitrile produced with above method.

SUMMARY OF THE INVENTION

Thus, an object of the present invention is to provide a method for producing xylylenediamine by hydrogenating phthalonitrile synthesized through ammoxidation of xylene, comprising recovering phthalonitrile, readily and at high yield, from a gas produced through ammoxidation, to thereby produce industrially efficiently xylylenediamine of high purity.

In an attempt to solve the aforementioned problems, the present inventors have carried out extensive studies focusing on the methodology for producing xylylenediamine, and have found that high purity xylylenediamine is obtained with high yield by trapping phthalonitrile contained in a gas produced through ammoxidation by an organic solvent; removing high-boiling-point impurities in a first distillation step; and in a second distillation step, separating the organic solvent and recovering phthalonitrile from the bottom of the column, hydrogenating phthalonitrile with specific solvent and liquid ammonia. The present invention has been accomplished on the basis of this finding.

Accordingly, the present invention provides a method for producing xylylenediamine by hydrogenating phthalonitrile separated from a gas produced by causing xylene to react with ammonia and oxygen-containing gas in the presence of a catalyst, which method comprises the following steps:

(1) a trapping step for bringing the gas into contact with an organic solvent, to thereby trap phthalonitrile in the organic solvent;

(2) a high-boiling-point impurity separation step for distilling a liquid in which phthalonitrile is trapped in the trapping step, to thereby recover phthalonitrile and the organic solvent from the top of the column and separate at the bottom of the column impurities having boiling points higher than that of phthalonitrile;

(3) a rectification step for subjecting phthalonitrile and the organic solvent resulting from the high-boiling-point impurity separation step to rectification, to thereby recover the organic solvent from the top of the column and recover liquefied phthalonitrile of high purity at the bottom of the column; and (4) a hydrogenation step for mixing high purity phthalonitrile with liquid ammonia and at least one solvent selected from aromatic hydrocarbon and saturated hydrocarbon, then subjecting hydrogenation of the phthalonitrile.

DETAILED DESCRIPTION OF PREFERRED EMBODIMENTS

Figure 1:
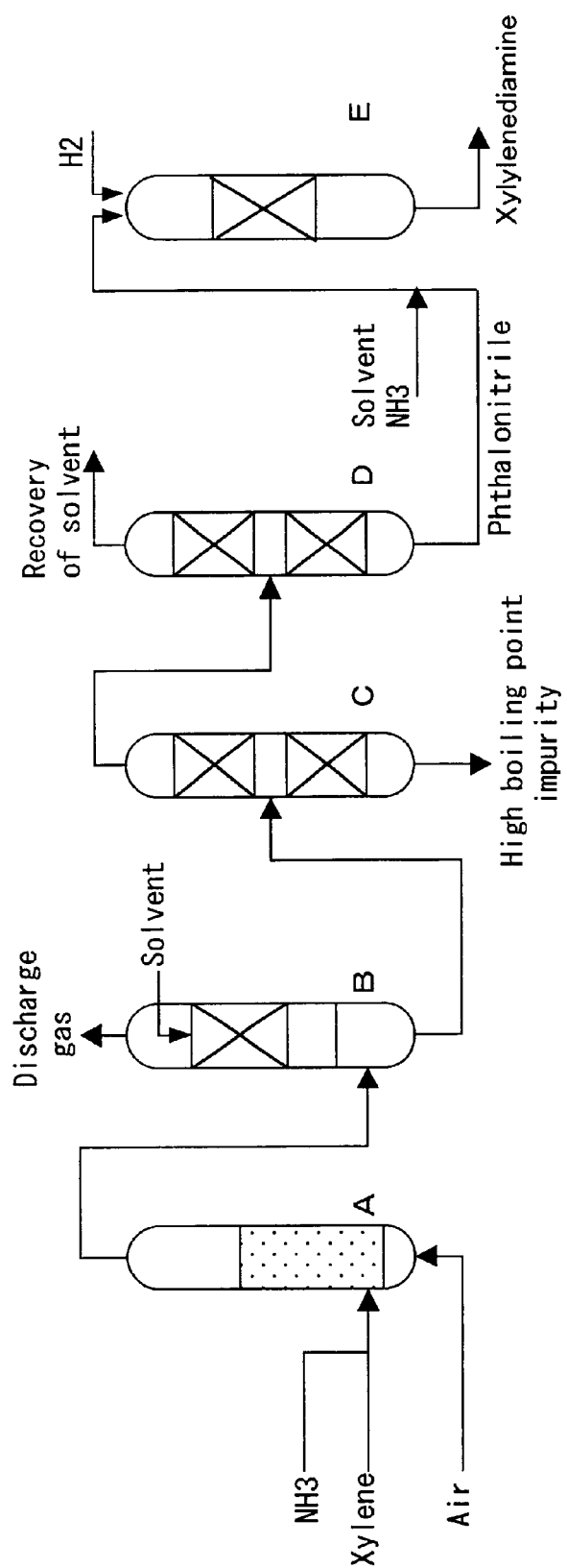
FIG. 1 is a flow chart illustrating one embodiment of the method for producing xylylenediamine according to the present invention, with A representing an ammoxidation reactor; B representing an phthalonitrile trapping column; C representing an high-boiling-point impurity separation column; D representing a rectification column; and E representing a hydrogenation reactor.

In the present invention, xylene is used as a raw material. Particularly, m-xylene and p-xylene are preferably used. Isophthalonitrile and terephthalonitrile are produced through ammoxidation of m-xylene and p-xylene, respectively, and, through the subsequent hydrogenation, isophthalonitrile and terephthaloitrile are converted into m-ylenediamine and p-xylylenediamine, respectively.

In the present invention, during ammoxidation in which xylene is caused to react with ammonia and an oxygen-containing gas, there can be used known catalysts such as a catalyst containing V—Cr—B—Mo oxide disclosed in Japanese Patent Application Laid-Open (kokai) No. Heisei 11(1999)-209332 and a catalyst containing Fe—Sb—V oxide disclosed in Japanese Patent Application Laid-Open (kokai) No. Heisei 9(1997)-71561.

The oxygen-containing gas to be used in ammoxidation is typically air, which may be enriched with oxygen. A diluent such as nitrogen or carbon dioxide gas may also be used in combination. Oxygen is used in an amount by mol at least three times, preferably 4–100 times that of xylene serving as a raw material. When the amount of oxygen is less than the lower limit, yield of phthalonitrile decreases, whereas when the amount is in excess of the upper limit, space-time yield decreases.

When ammoxidation is performed by use of air, the concentration of xyiene contained in a raw material gas to be fed to the reactor is 0.2–10 vol. %, preferably 0.5–5 vol. %. When the concentration is less than the lower limit, space-time yield decreases, whereas when the concentration is in excess of the upper limit, yield of phthalonitrile decreases.

Ammonia of industrial grade may be used as a raw material. Ammonia is used in an amount by mol of 2–20 times, preferably 6–15 times, that of xylene. When the amount of ammonia is less than the lower limit, yield of phthalonitrile decreases, whereas when the amount is in excess of the upper limit, space time yield decreases.

Since ammoxidation generates a large amount of heat of reaction, the reaction is carried out preferably in a gas-phase-fluidized manner so as to attain a uniform temperature profile in the reactor, and a variety of fluidized-bed reactors can be employed. Ammonia may be supplied in the form of a mixture with xylene. In this case, a portion of an oxygen-containing gas may be added to the mixture of ammonia and xylene, with care being exerted so that the composition of the mixture does not fall within the explosion region, and the resultant mixture may be supplied to the reactor.

The temperature of ammoxidation is 300–500° C., preferably 330–470° C. When the reaction temperature is lower than the lower limit, percent conversion decreases, whereas when the temperature is in excess of the upper limit, formation of by-products such as carbon dioxide gas and hydrogen cyanide gas increases, to thereby decrease the yield of phthalonitrile. Ammoxidation may be performed under ambient pressure, reduced pressure, or pressurized conditions, and a pressure of approximately ambient pressure to 0.2 MPa is preferred. Although the time of contact between the reactive gas and a catalyst varies in accordance with the conditions such as reaction temperature and the mol ratio of fed ammonia or oxygen-containing gas to fed xylene, the time is typically 0.3–30 seconds.

(1) Trapping Step

In the present invention, firstly in the trapping step, a gas produced through ammoxidation and supplied from the outlet of the ammoxidation reactor is introduced to a phthalonitrile trapping column, whereby the reactive gas is brought into contact with an organic solvent, to thereby dissolve phthalonitrile in the solvent. Thus, unreacted ammonia and gases such as hydrogen cyanide, carbon dioxide, steam, carbon monoxide, nitrogen, and oxygen are separated.

The organic solvent to be used is at least one solvent species selected from among alkylbenzenes, heterocyclic compounds, aromatic nitrites, and heterocyclic nitrites, and has a boiling point lower than that of phthalonitrile. Preferably, the organic solvent dissolves phthalonitrile therein at a high solubility, and is inert to phthalonitrile. An organic solvent of low boiling point increases the amount of solvent entrained with residual gas.

Examples of the organic solvent include m-xylene, p-xylene, pseudocumene, mesitylene, ethylbenzene, methylpyridines, benzonitrile, m-tolunitrile, p-tolunitrile and cyanopyridines. These compounds may be used singly or in combination. Of these, m-tolunitrile or p-tolunitrile is most suited in the present invention.

In operation of the phthalonitrile trapping column, the gas produced through ammoxidation is introduced into a liquid phase at the bottom of the column. The trapping column is operated under such a condition that the temperature of the liquid phase at the bottom of the column is lower than the boiling point of the bottom liquid. Although the pressure in the phthalonitrile trapping column may be ambient pressure, reduced pressure, or elevated pressure, a pressure of ambient pressure to pressure for ammoxidation is typically employed. Components which have not been absorbed in the organic solvent; e.g., ammonia, hydrogen cyanide, carbon dioxide, steam, carbon monoxide, nitrogen, and oxygen, are discharged from the top of the column, while phthalonitrile absorbed in the organic solvent is taken from the bottom of the column and forwarded to a high-boiling-point impurity separation step.

(2) High-Boiling-Point Impurity Separation Step and (3) Rectification Step

In the (2) high-boiling-point impurity separation step, phthalonitrile absorbed in the organic solvent undergoes distillation in a high-boiling-point impurity separation column. Thus, high-boiling-point impurities are separated from phthalonitrile and removed from the bottom potion of the column, and phthalonitrile and the organic solvent are recovered from the top of the column.

The recovered phthalonitrile and the organic solvent are forwarded to the (3) rectification step. The organic solvent and impurities having boiling points lower than that of phthalonitrile are separated and removed from the top of the column, while phthalonitrile in liquid form is recovered from the bottom of the column.

Supply from the high-boiling-point impurity separation column to the rectification column may be performed in a state of gas or a condensed liquid. However, the supply of gas state as generated vapor is advantageous, from the viewpoint of saving energy.

In the presence of impurities such as high-boiling-point by-products generated during ammoxidation, ammoxidation catalyst, and metallic components, phthalonitrile is unstable to heat, and is readily deteriorated to cause amidation, polymerization, or the like. This undesirable change results in a loss of some amounts of phthalonitrile during distillation, and the loss increases in proportion to the period of time during which crude phthalonitrile is handled at high temperature and to the handling temperature. Thus, in order to obtain phthalonitrile at high yield, separation of high-boiling-point impurities must be performed as rapidly as possible and at as low a temperature as possible.

According to the present invention, phthalonitrile is separated in advance from high-boiling-point impurities in the high-boiling-point impurity separation step. Thus, the period of time during which phthalonitrile contacts the high-boiling-point impurities under heat can be shortened. In addition, distillation can be performed in a high vacuum, to thereby lower the temperature in the high-boiling-point impurity separation column and prevent deterioration of phthalonitrile.

In each column, distillation is carried out under reduced pressure. The pressure is predetermined such that phthalonitrile is not deposited in the column.

In general, when a mixture containing a sublimable high-melting-point substance is subjected to distillation, the interior temperature of the distillation column is elevated to a temperature not lower than the melting point of the substance, to thereby prevent plugging caused by deposition of crystals. Moreover, in the case in which a sublimable high-melting-point substance and a solvent in an amount sufficient for dissolving the sublimable high-melting-point substance are together placed in the distillation column, deposition of crystals does not occur even through the operation temperature is not higher than the melting point of the substance.

The distribution of phthalonitrile concentration in a distillation column is determined in accordance with the composition of supplied liquid, conditions for distillation and separation of the bottom residue, and vapor-liquid equilibrium conditions, and the temperature profile varies in accordance with operation pressure. Since the solubility of phthalonitrile in a solvent is univocally determined only by temperature, operation pressure affects phthalonitrile to be deposited or not deposited in the distillation column. For example, when rectification of isophthalonitrile is carried out by use of m-tolunitrile serving as an organic solvent for trapping a target with the inside pressure of the rectification column being 4.2 kPa or lower, in the distillation column there is generated a region where the temperature is not higher than the melting point of isophthalonitrile and the isophthalonitrile concentration exceeds the solubility of isophthalonitrile in m-tolunitrile. In this region, isophthalonitrile is deposited, to thereby plug the column.

In the case in which phthalonitrile and an organic solvent are supplied in the form of vapor from the high-boiling-point impurity separation column to the rectification column, increase in pressure of the top of the rectification column requires a higher bottom temperature of the high-boiling-point impurity separation column, leading to an increase in the amount of deteriorated phthalonitrile. Thus, the operation pressure of the distillation column is controlled to high vacuum within the range where phthalonitrile is not deposited in the distillation column. Specifically, when m-tolunitrile is used as an organic solvent for trapping isophthalonitrile, the pressure in the distillation column is preferably 5–10 kPa.

According to the method of the present invention, no scrubber is required to be provided between the condensation system and the vacuum-evacuation system. This is because phthalonitrile is in contact with a solvent in an amount sufficient for dissolving therein in the distillation column, and substantially no vapor pressure of phthalonitrile, caused by a low temperature of the condensation section predominantly containing a solvent, prevents migration of phthalonitrile to the vacuum-evacuation system.

According to the method of the present invention, impurities having boiling points higher than that of phthalonitrile and contained in the gas produced through ammoxidation are removed by means of the high-boiling-point impurity separation column, and as a result, these impurities do not migrate into the rectification column. Thus, phthalonitrile is subjected to high temperature in the co-presence of a substance which promotes deterioration of phthalonitrile only for a limited time; i.e., only when phthalonitrile is retained in the high-boiling-point impurity separation column, leading to a reduction in loss of phthalonitrile caused by deterioration.

(4) Hydrogenation Step

The high purity phthalonitrile from the bottom of rectification column is subjected hydrogenation in a solution state after mixing with liquid ammonia and a solvent.

At least one solvent selected from aromatic hydrocarbon and saturated hydrocarbon is used as a solvent for the hydrogenation of phthalonitrile. The solvent exemplified benzene, toluene, m-xylene, p-xylene, mesitylene, pseudocumene, hexane and cyclohexane. These solvents may be used singly or in combination of two or more species. Of these, m-xylene or p-xylene is advantageously used since the number of compounds used in the plant is reduced.

In the hydrogenation step, production of xylylenediamine through hydrogenation of phthalonitrile is preferably carried out by use of a catalyst predominantly containing nickel and/or cobalt. Hydrogenation of phthalonitrile in the presence of ammonia may be carried out by use of a platinum-group catalyst. However, when a platinum-group catalyst such as a ruthenium catalyst is used, nucleus hydrogenation of produced xylylenediamine and an aromatic hydrocarbon (e.g. m-xylylene, p-xylylene, mesitylene or pseudocumene) serving as the organic solvent proceeds, which is undesirable.

The composition of the raw material to be fed to a hydrogenation reactor is appropriately determined arbitrarily. When the concentration of phthalonitrile serving as a reactant is lower and when the concentration of ammonia serving as a solvent is higher, the yield of xylylenediamine becomes higher. In order to attain satisfactory yield and productivity, the composition of the raw material is regulated through further addition of the solvent or ammonia. The composition of the raw material is preferably determined so as to attain the following compositional proportions: phthalonitrile (1–10 wt. %), the solvent (1–79 wt. %), and ammonia (20–98 wt. %).

Hydrogenation may be carried out in a batch-type process or a continuous process. In a batch-type process, hydrogenation may be carried out in a tank reactor in which the raw material is completely mixed with a powdery catalyst of a Raney metal such as nickel or cobalt. Industrially, hydrogenation is carried out in a simple manner through a method employing a trickle-type continuous reactor including a tubular reactor and a molded catalyst provided on a fixed bed, in which the raw material solution and hydrogen gas are fed in parallel through the upper section of the reactor.

A catalyst comprising nickel and/or cobalt supported on a carrier is preferably used as a hydrogenation catalyst. Examples of the carrier employed include diatomaceous earth, silicon oxide, alumina, silica-alumina, titanium oxide, zirconium oxide, and carbon.

When a nickel catalyst is used as a hydrogenation catalyst, the reaction temperature is 60–130° C., and the reaction pressure is 4–15 MPa.

A reaction mixture containing xylylenediamine is obtained through the aforementioned hydrogenation. High purity xylylenediamine can be obtained by separating ammonia, solvent and some byproducts from the reaction mixture. This separation is preferably carried out through distillation.

The method of the present invention will next be described in detail with reference the drawing. FIG. 1 is a flow chart illustrating one embodiment of the method for purifying phthalonitrile according to the present invention. However, the present invention is not limited by this drawing.

In FIG. 1, a gas produced in an ammoxidation reactor A is supplied to a phthalonitrile trapping column B. In the upper section of the trapping column, an absorption portion comprising plates or a packed layer is provided, and an organic solvent is fed through the upper section of the trapping column. By bringing the gas into contact with the organic solvent, phthalonitrile and high-boiling-point impurities contained in the produced gas are trapped in the solvent. Components which have not been absorbed in the organic solvent; e.g., ammonia, hydrogen cyanide, carbon dioxide, steam, carbon monoxide, nitrogen, and oxygen, are discharged from the upper section of the column.

The organic liquid containing phthalonitrile is transferred to a high-boiling-point impurity separation column C, whereby phthalonitrile and the organic solvent are recovered from the top, and high-boiling-point impurities are discharged from the bottom. The recovered phthalonitrile and the organic solvent are transferred to a rectification column D. The organic solvent is recovered from the top of the column, while phthalonitrile is recovered from the bottom of the column. Then the phthalonitrile from the bottom of rectification column is sent to a hydrogenation reactor E and subjected hydrogenation in a solution state after mixing with liquid ammonia and a solvent. High purity phthalonitrile is obtained by the rectification of the hydrogenation product using distillation column.

In the present invention, xylylenediamine of high purity is produced industrially efficiently at high yield by hydrogenating phthalonitrile separated from a bottom of a distillation column which rectify phthalonitrile trapped from ammoxidation gas.

EXAMPLES

The present invention will next be described in more detail by way of Example, which should not be construed as limiting the invention thereto.

In the below-described Examples, analysis of the compositions was carried out by means of gas chromatography.

Preparation of Catalyst for Ammoxidation Reaction

Vanadium pentoxide ($V_2O_5$) (229 g) was added to water (500 mL), to thereby yield a mixture, and an aliquot of oxalic acid (477 g) was added to the mixture with stirring at 80–90° C. so as to dissolve the vanadium compound, to thereby yield a solution of vanadium oxalate. Another aliquot of oxalic acid (963 g) was added to water (400 mL), and the resultant mixture was heated to 50–60° C. To the mixture, a solution of chromic anhydride ($CrO_3$) (252 g) in water (200 mL) was added under sufficient stirring so as to dissolve the components, to thereby yield a solution of chromium oxalate. The thus-yielded solutions were mixed at 50–60° C., to thereby prepare a V—Cr-containing solution. To the V—Cr-containing solution, a solution of phosphomolybdic acid ($H_3(PMo_{12}O_{40}) \cdot 20H_2O$) (41.1 g) dissolved in water (100 mL) and a solution of potassium acetate ($CH_3COOK$) (4.0 g) dissolved in water (100 mL) were added. Subsequently, a 20 wt. % aqueous silica sol (containing 0.02 wt. % of $Na_2O$) (2,500 g) was added, to thereby yield a slurry.

Boric acid ($H_3BO_3$) (78 g) was added to the slurry, and the resultant mixture was concentrated by heating until the liquid amount became approximately 3,800 g. The thus-concentrated mixture containing catalyst components was dried by use of a spray drier while the inlet temperature and the outlet temperature were maintained at 250° C. and 130° C., respectively. The dried mixture was further dried by means of a drier at 130° C. for 12 hours, and the resultant mixture was calcined at 400° C. for 0.5 hours and at 550° C. for eight hours under air flow, to thereby obtain a catalyst to be used in a fluidized process. The obtained catalyst was found to have atomic proportions of V:Cr:B:Mo:P:Na:K= 1:1:0.5:0.086:0.007:0.009:0.020 and an effective catalyst component content of 50 wt. %.

Example 1

Ammoxidation; trapping of isophthalonitrile in an organic solvent; distillation for separating and purifying isophthalonitrile and hydrgenation of the isophthalonitrile were performed on the basis of the process flow shown in FIG. 1.

The catalyst (6 L) which had been prepared in the above-described manner was charged into an ammoxidation reactor A. After air, m-xylene (MX), and ammonia had been mixed and pre-heated to 350° C., the resultant mixture was fed to the reactor. The following feed conditions were employed: an amount of fed MX of 350 g/Hr; a mol ratio of $NH_3$/MX of 11; a mol ratio of $O_2$/MX of 5.4; and an SV of 630 $Hr^{-1}$. The temperature and the pressure for reaction were 420° C. and 0.2 MPa-G, respectively.

The gas produced through reaction and supplied from the top of the reactor was introduced into an phthalonitrile trapping column B, whereby isophthalonitrile contained in the produced gas was trapped in m-tolunitrile serving as a solvent.

The phthalonitrile trapping column, made of SUS 304, was equipped with a condenser at the upper section and a gas-bubbling inlet at the bottom section. The main body of the column had an inside diameter of 100 mm and a height of 800 mm, and the lower portion (450 mm) of the main body was provided with a double tube structure so as to allow steam heating.

Specifically, the gas produced through the aforementioned ammoxidation was subjected to a trapping process for two hours by use of m-tolunitrile (2 kg) charged into the trapping column and heated to 175° C., to thereby trap components. After completion of trapping, the liquid was found to have the following composition; i.e., m-tolunitrile (73.5 wt. %), isophthalonitrile (25 wt. %), 3-cyanobenzamide (1 wt. %), and other components (0.5 wt. %).

The aforementioned liquid was supplied to a middle stage plate of a high-boiling-point impurity separation column C, and the gas produced through distillation carried out in the high-boiling-point impurity separation column C was supplied to a rectification column D. Distillation in the high-boiling-point impurity separation column C was performed at a top pressure of 8 kPa, a top temperature of 164° C., and a bottom temperature of 204° C., and distillation in the rectification column D was performed at a top pressure of 6 kPa, a top temperature of 120° C., and a bottom temperature of 183° C. The thus-purified isophthalonitrile, which had been recovered from the bottom of the rectification column, had a purity of 99.93%. The percent recovery of isophthalonitrile including isophthalonitrile contained in a fraction from which the high-boiling-point impurity had been separated was 98%. In other words, the high-boiling-point impurity included 2% unrecovered isophthalonitrile.

Liquid ammonia and m-xyiene are mixed with the isophthalonitrile recovered from the bottom of the rectification column to use as raw material for the hydrogenation. The proportions of isophthalonitrile/m-xylene/ammonia in the solution were 5/10/85 by weight.

An Ni/diatomaceous earth catalyst (Ni content: 50 wt. %) (5 kg) was charged into vertical tubular hydrogenation reactor E (volume: 4 L). Through the upper section of the reactor, a raw material containing isophthalonitrile, m-xylene, and ammonia was fed at a rate of 6 kg/hr. Hydrogen was fed through the upper section of the reactor in parallel with the raw material, and hydrogenation was carried out at a reaction pressure of 12 MPa and at 90° C.

Through hydrogenation, the yield of m-xylylenediamine was 96.5% on the basis of isophthalonitrile.

The hydrogenation product was subjected to distillation removing ammonia and m-xylene. Then high- and low-boiling-point components were removed by distillation. The obtained m-xylylenediamine had a purity of 99.99 wt. %, and was found to contain 3-methylbenzylamine (16 ppm), unknown low-boiling-point components (12 ppm).

What is claimed is:

1. A method for producing xylylenediamine by hydrogenating phthalonitrile separated from a gas produced by causing xylene to react with ammonia and oxygen-containing gas in the presence of a catalyst, which method comprises the following steps:

(1) a trapping step for bringing the gas into contact with an organic solvent, to thereby trap phthalonitrile in the organic solvent;

(2) a high-boiling-point impurity separation step for distilling a liquid in which phthalonitrile is trapped in the trapping step, to thereby recover phthalonitrile and the organic solvent from the top of the column and separate at the bottom of the column impurities having boiling points higher than that of phthalonitrile;

(3) a rectification step for subjecting phthalonitrile and the organic solvent resulting from the high-boiling-point impurity separation step to rectification, to thereby recover the organic solvent from the top of the column and recover liquefied phthalonitrile of high purity at the bottom of the column; and (4) a hydrogenation step for mixing high purity phthalonitrile with liquid ammonia and at least one solvent selected from aromatic hydrocarbon and saturated hydrocarbon, then subjecting hydrogenation of the phthalonitrile.

2. A method for producing xylylenediamine according to claim 1, wherein the phthalonitrile and organic solvent resulting from the high-boiling-point impurity separation step are supplied in the form of vapor to a rectification column employed in the rectification step.

3. A method for producing xylylenediamine according to claim 1, wherein the organic solvent for trapping phthalonitrile is at least one compound selected from among alkylbenzenes, heterocyclic compounds, aromatic nitrites, and heterocyclic nitrites.

4. A method for producing xylylenediamine according to claim 1, wherein a nickel catalyst and/or a cobalt catalyst is employed in the hydrogenation step.

5. A method for producing xylylenediamine according to claim 4, wherein a nickel and/or cobalt is supported on at least one carrier selected from among diatomaceous earth, silicon oxide, alumina, silica-alumina, titanium oxide, zirconium oxide, and carbon.

6. A method for producing xylylenediamine according to claim 1, wherein the solvent for hydrogenation step is at least one compound selected from among benzene, toluene, m-xylene, p-xylene, mesitylene, pseudocumene, hexane and cyclohexane.

* * * * *